(12) United States Patent
Johnson et al.

(10) Patent No.: US 10,744,337 B2
(45) Date of Patent: Aug. 18, 2020

(54) PHOTOBIOMODULATION THERAPY TO REDUCE THE EFFECTS OF FIBROMYALGIA

(71) Applicant: MULTI RADIANCE MEDICAL, Solon, OH (US)

(72) Inventors: Douglas Johnson, Brownstown, MI (US); Max Kanarsky, Solon, OH (US); Ernesto Leal-Junior, Sao Paulo (BR)

(73) Assignee: MULTI RADIANCE MEDICAL, Solon, OH (US)

( * ) Notice: Subject to any disclaimer, the term of this patent is extended or adjusted under 35 U.S.C. 154(b) by 0 days.

(21) Appl. No.: 16/325,825

(22) PCT Filed: Apr. 13, 2018

(86) PCT No.: PCT/US2018/027523
§ 371 (c)(1),
(2) Date: Feb. 15, 2019

(87) PCT Pub. No.: WO2018/191640
PCT Pub. Date: Oct. 18, 2018

(65) Prior Publication Data
US 2020/0086134 A1      Mar. 19, 2020

Related U.S. Application Data

(60) Provisional application No. 62/485,107, filed on Apr. 13, 2017.

(51) Int. Cl.
*A61N 2/00* (2006.01)
*A61N 5/06* (2006.01)
(Continued)

(52) U.S. Cl.
CPC ............ *A61N 2/008* (2013.01); *A61N 2/002* (2013.01); *A61N 2/06* (2013.01); *A61N 5/0618* (2013.01);
(Continued)

(58) Field of Classification Search
CPC .......... A61N 2/008; A61N 2/002; A61N 2/06; A61N 5/0618; A61N 5/0622;
(Continued)

(56) References Cited

U.S. PATENT DOCUMENTS

| 4,646,743 A | * | 3/1987 | Parris | ................... A61N 5/06 |
|---|---|---|---|---|
| | | | | 250/495.1 |
| 2002/0103454 A1 | | 8/2002 | Sackner et al. | |

(Continued)

OTHER PUBLICATIONS

International Search Report and Written Opinion dated Jul. 26, 2018 for Application No. PCT/US18/27523.
(Continued)

*Primary Examiner* — Navin Natnithithadha
*Assistant Examiner* — Sunita Reddy
(74) *Attorney, Agent, or Firm* — Tarolli, Sundheim, Covell & Tummino LLP

(57) ABSTRACT

Photobiomodulation therapy (PBMT) can be applied to a tender area on a subject's body to treat fibromyalgia. A light source device can be contacted to a subject's skin proximal to a tender area on the subject's body. A light signal (with wavelengths from the red to infrared part of the spectrum) can be applied in at least one of a pulsed operating mode, a continuous operating mode, and a super-pulsed operating mode through the light source device to the tender area. The light signal is applied for a time sufficient to stimulate a phototherapeutic response in the tender area to treat fibromyalgia.

19 Claims, 12 Drawing Sheets

(51) Int. Cl.
*A61N 2/06* (2006.01)
*A61N 5/067* (2006.01)

(52) U.S. Cl.
CPC ...... *A61N 5/0622* (2013.01); *A61N 2005/067* (2013.01); *A61N 2005/0632* (2013.01); *A61N 2005/0659* (2013.01); *A61N 2005/0663* (2013.01)

(58) Field of Classification Search
CPC .... A61N 2005/0632; A61N 2005/0659; A61N 2005/0663; A61N 2005/067
USPC ...................................................... 600/9–15
See application file for complete search history.

(56) References Cited

U.S. PATENT DOCUMENTS

| | | | |
|---|---|---|---|
| 2003/0167080 A1* | 9/2003 | Hart | A61N 5/0616 607/88 |
| 2004/0073079 A1* | 4/2004 | Altshuler | A61N 7/00 600/1 |
| 2004/0158300 A1* | 8/2004 | Gardiner | A61N 5/0619 607/88 |
| 2005/0177093 A1* | 8/2005 | Barry | A61N 5/0616 604/20 |
| 2005/0182460 A1* | 8/2005 | Kent | A61N 5/0616 607/88 |
| 2005/0278003 A1* | 12/2005 | Feldman | A61M 21/02 607/88 |
| 2005/0283145 A1 | 12/2005 | Malak | |
| 2006/0030908 A1* | 2/2006 | Powell | A61N 5/0616 607/88 |
| 2006/0047330 A1* | 3/2006 | Whatcott | A61N 5/0616 607/89 |
| 2006/0111761 A1* | 5/2006 | Butler | A61N 5/0613 607/88 |
| 2006/0129022 A1* | 6/2006 | Venza | A61N 2/008 600/13 |
| 2006/0206173 A1* | 9/2006 | Gertner | A61N 5/0616 607/88 |
| 2006/0247741 A1* | 11/2006 | Hsu | A61N 5/0616 607/88 |
| 2006/0287696 A1* | 12/2006 | Wright | A61N 5/0613 607/88 |
| 2007/0167999 A1* | 7/2007 | Breden | A61N 5/06 607/88 |
| 2007/0208396 A1* | 9/2007 | Whatcott | A61N 5/0613 607/88 |
| 2008/0140164 A1* | 6/2008 | Oberreiter | A61N 5/0616 607/88 |
| 2009/0005631 A1* | 1/2009 | Simenhaus | A61N 2/002 600/9 |
| 2009/0234343 A1* | 9/2009 | Behrakis | A61B 18/203 606/9 |
| 2009/0254155 A1 | 10/2009 | Kanarsky | |
| 2010/0087898 A1* | 4/2010 | Clement | A61N 5/0616 607/88 |
| 2010/0179469 A1* | 7/2010 | Hammond | A61N 5/0603 604/20 |
| 2011/0004201 A1* | 1/2011 | Nuijs | A61B 18/203 606/9 |
| 2011/0144729 A1 | 6/2011 | Weber | |
| 2012/0046716 A1* | 2/2012 | Dougal | A61N 5/0613 607/91 |
| 2013/0344454 A1* | 12/2013 | Nath | A61N 5/0616 433/29 |
| 2014/0288351 A1 | 9/2014 | Jones | |
| 2015/0134032 A1* | 5/2015 | Chicchi | A61N 5/0613 607/89 |
| 2016/0192988 A1* | 7/2016 | Albright | A61B 18/22 606/11 |
| 2016/0235980 A1* | 8/2016 | Berman | A61N 1/40 |
| 2016/0296764 A1* | 10/2016 | Bellinger | A61N 5/0616 |

OTHER PUBLICATIONS

Multi Radiance Medical "Technology", www.multiradiance.com, published on Mar. 11, 2017, retrieved on Jun. 18, 2018, accessed at <https://web.archive.org/web/20170311032815/https://multiradiance.com/technology/>.

Allen, "Physical agents used in the management of chronic pain by physical therapists." Physical medicine and rehabilitation clinics of North America 17.2 (2006): 315-345.

Bardal, "Aerobic and cardiovascular autonomic adaptations to moderate intensity endurance exercise in patients with fibromyalgia." Journal of rehabilitation medicine 47.7 (2015): 639-646.

Bircan, "Effects of muscle strengthening versus aerobic exercise program in fibromyalgia." Rheumatology International 28.6 (2008): 527-532.

Burckhardt, "A randomized, controlled clinical trial of education and physical training for women with fibromyalgia." The Journal of Rheumatology 21.4 (1994): 714-720.

Busch, "Exercise therapy for fibromyalgia." Current pain and headache reports 15.5 (2011): 358.

Wright, "Management and treatment of temporomandibular disorders: a clinical perspective." Journal of Manual & Manipulative Therapy 17.4 (2009): 247-254.

Cidral-Filho, "Light-emitting diode therapy induces analgesia in a mouse model of postoperative pain through activation of peripheral opioid receptors and the L-arginine/nitric oxide pathway." Lasers in medical science 29.2 (2014): 695-702.

Alonso-Blanco, "Characteristics of referred muscle pain to the head from active trigger points in women with myofascial temporomandibular pain and fibromyalgia syndrome." The journal of headache and pain 13.8 (2012): 625-637.

De Boever, "Recommendations for examination, diagnosis, management of patients with temporomandibular disorders and orofacial pain by the general dental practitioner." J Orofac Pain 22 (2008): 266-278.

De Carvalho, "Effect of low-level laser therapy on pain, quality of life and sleep in patients with fibromyalgia: study protocol for a double-blinded randomized controlled trial." Trials 13.1 (2012): 221.

Dworkin, "Research diagnostic criteria for temporomandibular disorders: review, criteria, examinations and specifications, critique." J Craniomandib Disord 6 (1992): 301-355.

Emshoff, "Low-level laser therapy for treatment of temporomandibular joint pain: a double-blind and placebo-controlled trial." Oral Surgery, Oral Medicine, Oral Pathology, Oral Radiology, and Endodontology 105.4 (2008): 452-456.

World Medical Association. "World Medical Association Declaration of Helsinki: ethical principles for medical research involving human subjects." Jama 310.20 (2013): 2191.

Goldenberg, "Management of fibromyalgia syndrome." Jama 292.19 (2004): 2388-2395.

Gur "Efficacy of low power laser therapy in fibromyalgia: a single-blind, placebo-controlled trial." Lasers in medical science 17.1 (2002): 57-61.

Haas, "(544) Interdisciplinary pain rehabilitation for fibromyalgia: gender differences in immediate and long-term outcomes." The Journal of Pain 15.4 (2014): S112.

Herpich, "Effects of phototherapy on muscle activity and pain in individuals with temporomandibular disorder: a study protocol for a randomized controlled trial." Trials 15.1 (2014): 491.

Herranz-Aparicio, "The use of low level laser therapy in the treatment of temporomandibular joint disorders. Review of the literature." Medicina oral, patologia oral y cirugia bucal 18.4 (2013): e603.

Kalamir, "Intra-oral myofascial therapy versus education and self-care in the treatment of chronic, myogenous temporomandibular disorder: a randomised, clinical trial." Chiropractic & manual therapies 21.1 (2013): 17.

Laakso, "Plasma ACTH and β-endorphin levels in response to low level laser therapy (LLLT) for myofascial trigger points." Laser Therapy 6.3 (1994): 133-141.

(56) References Cited

OTHER PUBLICATIONS

Da Silva, "Effects of exercise training and photobiomodulation therapy (Extraphoto) on pain in women with fibromyalgia and temporomandibular disorder study protocol for a randomized controlled trial." Trials 16.1 (2015): 252.
John, "Reliability of clinical temporomandibular disorder diagnoses." Pain 118.1-2 (2005): 61-69.
Stucki, "Physical therapy in the treatment of fibromyalgia." Scandinavian journal of rheumatology 29.113 (2000): 78-85.
Pedroni, "Prevalence study of signs and symptoms of temporomandibular disorders in university students." Journal of oral rehabilitation 30.3 (2003): 283-289.
Pereira, "Efficacy of red and infrared lasers in treatment of temporomandibular disorders—a double-blind, randomized, parallel clinical trial." CRANIO® 32.1 (2014): 51-56.
Chalaye, "The role of cardiovascular activity in fibromyalgia and conditioned pain modulation." PAIN® 155.6 (2014): 1064-1069.
Brandt, "Perfil de humor de mulheres com fibromialgia." J Bras Psiquiatr 60.3 (2011): 216-20.
Wolfe, "The American College of Rheumatology preliminary diagnostic criteria for fibromyalgia and measurement of symptom severity." Arthritis care & research 62.5 (2010): 600-610.
Sattayut, "A study of the influence of low intensity laser therapy on painful temporomandibular disorder patients." Laser therapy 21.3 (2012): 183-192.
Serra, "Correlation of six-minute walking performance with quality of life is domain-and gender-specific in healthy older adults." PLoS one 10.2 (2015): e0117359.
Teixiera, "Chronic pain and depression. Rev Neurocienc 2006; 14 (2): 044-053." Pain 2 (1976): 361-378.
Vinck, "Evidence of changes in sural nerve conduction mediated by light emitting diode irradiation." Lasers in Medical Science 20.1 (2005): 35-40.
Walitt, "Selective serotonin reuptake inhibitors for fibromyalgia syndrome." Sao Paulo Medical Journal 133.5 (2015): 454-454.
Wang, "Fibromyalgia diagnosis: a review of the past, present and future." Expert review of neurotherapeutics 15.6 (2015): 667-679.

\* cited by examiner

PHOTOBIOMODULATION THERAPY TO REDUCE THE EFFECTS OF FIBROMYALGIA

CROSS-REFERENCE TO RELATED APPLICATIONS

This application is a national stage entry of PCT Appl. No. PCT/US2018/027523, filed Apr. 13, 2018, entitled "PHOTOBIOMODULATION THERAPY TO REDUCE THE EFFECTS OF FIBROMALGIA", which claims the benefit of U.S. Provisional Application No. 62/485,107, filed Apr. 13, 2017, entitled "SYSTEM OF CONCURRENT USE OF LASERS AND LEDS AND METHOD FOR THE REDUCTION OF PAIN ASSOCIATED WITH FIBROMYALGIA". These applications are hereby incorporated by reference in their entirety for all purposes.

TECHNICAL FIELD

The present disclosure relates generally to photobiomodulation therapy (PBMT) and, more specifically, to systems and methods that apply PBMT to a tender area on a subject's body to treat fibromyalgia (FM).

BACKGROUND

Fibromyalgia (FM) is a non-inflammatory syndrome characterized by chronic musculoskeletal pain. In patients suffering from FM, the brain and spinal cord process pain sensations abnormally by lowering the threshold at which stimuli cause pain or discomfort. As such, stimuli, which normally would not cause pain, would be amplified in a patient suffering from FM and cause debilitating pain. In many cases, FM can be accompanied by fatigue, sleep, memory, cognitive difficulties, and/or mood issues. Many subjects suffering from fibromyalgia also have tension headaches, migraines, temporomandibular joint (TMJ) disorder, irritable bowel syndrome, interstitial cystitis or painful bladder syndrome, anxiety, and/or depression. These symptoms can be reduced to some degree through medications. Additionally, patients frequently use alternative therapies, like stress management and exercise, to reduce the symptoms as an alternative to or in addition to the medications with varying levels of success. Accordingly, there is a need for a non-pharmacological treatment that can further reduce the symptoms of FM.

SUMMARY

The present disclosure relates generally to photobiomodulation therapy (PBMT) and, more specifically, to systems and methods that apply PBMT to a tender area on a subject's body to treat fibromyalgia (FM). PBMT provides a non-pharmacological treatment for fibromyalgia that can be used alone or in combination with medications and/or alternative therapies, like stress management or exercise.

In one aspect, the present disclosure can include a method for applying PBMT to a patient diagnosed with FM to treat FM. A light source device can be contacted to a subject's skin proximal to a tender area on the subject's body. A light signal can be applied in at least one of a pulsed operating mode, a continuous operating mode, and a super-pulsed operating mode through the light source device to the tender area. The light signal is applied for a time sufficient to stimulate a phototherapeutic response in the tender area.

In another aspect, the present disclosure can include a light source device to applying PBMT to a patient diagnosed with FM to treat FM. The light source device can be configured to contact a subject's skin proximal to a tender area on the subject's body and includes a cluster of light delivery sources, a permanent magnet, a processing unit, and a power source. The cluster of light delivery sources can include: a first light source configured to generate a first portion of a light signal with a wavelength from 890-910 nm in a super-pulsed operating mode; a second light source configured to generate a second portion of the light signal with a wavelength from 600-700 nm in a pulsed operating mode or a continuous operating mode; and a third light source configured to generate a third portion of the light signal with a wavelength from 810-880 in the pulsed operating mode or the continuous operating mode. The permanent magnet can provide a constant magnetic field from 5 mT to 1 T. The processing unit can be preprogrammed with a time for application of the light signal to the tender area.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
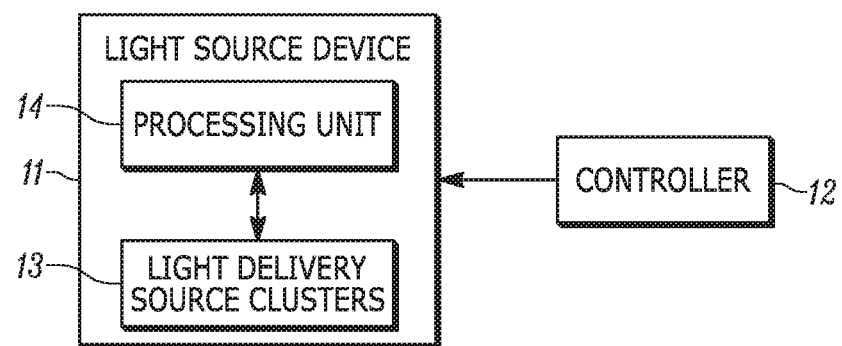
FIG. 1 is a block diagram illustration showing an example of a system that configures and applies a photobiomodulation therapy (PBMT) to a tender area on a subject's body to treat fibromyalgia (FM) in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising" can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "photobiomodulation" refers to the application of a light signal to a portion of a subject's body to induce a phototherapeutic response in cells within the portion of the subject's body.

As used herein, the term "photobiomodulation therapy (PBMT)" refers to a drug-free, non-invasive treatment procedure, in which a light signal is applied to a certain region of a subject's body to treat a certain medical condition (e.g., pain, injury, disorder, disease, or the like) via a phototherapeutic response. In some instances, PBMT can be used alone to induce a phototherapeutic response, but in other instances, PBMT can be used in combination with medications and/or alternative therapies, like stress management or exercise, to achieve a more favorable treatment outcome.

As used herein, the term "light signal" refers to light having at least one wavelength. However, the light signal may include a combination of lights having wavelengths that create a synergistic effect when combined and improve the percentage of available light at greater tissue depths. In some instances, the wavelengths can be within a wavelength range of 600-1100 nm. For example, the wavelengths can include at least one wavelength corresponding to the visible range of the electromagnetic spectrum (e.g., red light) and at least one wavelength corresponding to the near-infrared or infrared range of the electromagnetic spectrum.

As used herein, the term "light source device" refers to a mechanical implement that can deliver a light signal of PMBT to a portion of the subject's body. Examples of the light source device include a probe, a flexible array device, or the like.

As used herein, the term "light source" refers to a component of a light source device that delivers one or more lights of different wavelengths. For example, the light source can be a low-level laser source (e.g., a laser light emitting diode (LED)) that generates coherent light. The low-level laser source can operate in a super pulsed mode that generates ultrashort pulses with a high peak power and minimal heat. As another example, the light source can be an incoherent light source, such as a traditional LED or light bulb. The incoherent light source can operate in a pulsed mode and/or a continuous mode.

As used herein, the term "phototherapeutic response" refers to a biological response to application of PBMT to a portion of the subject's body. The biological response can be the creation of a neural blockade to block one or more nocioreceptive pathways to improve a subject's sensitivity to pain.

As used herein, the term "tender area" refers to a portion of a subject's body that experiences pain or discomfort when touched. In some instances, the tender area can include one or more "tender points", which refers to an extremely sensitive spot on the body, not on a joint itself, which elicits pain in response to application of pressure. Tender points can occur on both the left and right side of the subject's body and can be located in a low cervical region of the subject's body, a second rib of the subject's body, an occiput region of the subject's body, a trapezius muscle of the subject's body, a supraspinatus region of the subject's body, a lateral epicondyle region of the subject's body, a gluteal region of the subject's body, a greater trochanter region of the subject's body, and knee region of the subject's body.

As used herein, the term "treatment" refers to medical care given to a subject to heal or cure a medical condition, like fibromyalgia. The terms "treatment" and "therapy" can be used interchangeably herein.

As used herein, the term "proximal" refers to a location that is near a target. For example, a device that is located proximal a tender area can be located over the tender area, but need not be directly over the center of the tender area.

As used herein, the term "sufficient" refers to an amount adequate enough to satisfy a condition. For example, "a time sufficient to stimulate a phototherapeutic response in a tender area" can refer to a light signal being applied to the tender area for a time adequate enough to stimulate the phototherapeutic response.

As used herein, the term "direct" refers to the absence of intervening elements. For example, a device that directly contacts a skin surface has no intervening elements between the device and the skin surface. When the term "contact" is used herein, it means "direct contact" unless otherwise stated.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to photobiomodulation therapy (PBMT) and, more specifically, to systems and methods that apply PBMT to a tender area on a subject's body to treat fibromyalgia (FM). PBMT provides a non-pharmacological therapy to patients suffering from FM. The PBMT can be used alone or in combination with a pharmaceutical treatment and/or an alternative treatment (like stress management or exercise) to manage the symptoms of FM.

FM, more often afflicting women, is characterized by chronic, widespread musculoskeletal pain. The pain can be accompanied by fatigue, sleep, memory, cognitive difficulties, and/or mood issues. PBMT can be applied to a tender area in a transcutaneous and non-invasive manner. Tender areas can occur on both the left and right side of the subject's body and can include tender points, which can be located in a low cervical region of the subject's body, a second rib of the subject's body, an occiput region of the subject's body, a trapezius muscle of the subject's body, a supraspinatus region of the subject's body, a lateral epicondyle region of the subject's body, a gluteal region of the subject's body, a greater trochanter region of the subject's body, and knee region of the subject's body. By applying the PBMT to a portion of the subject's body proximal to the tender area, a biological response can be triggered, leading to the creation of a neural blockade to block nocioreceptive pathways. Such a neural blockade improves a subject's sensitivity to pain, leading to an improvement in a subject's overall quality of life.

III. Photobiomodulation Therapy (PBMT)

PBMT provides a non-pharmacological therapy that can be administered to a patient in a non-invasive manner to stimulate a phototherapeutic response. As used herein, a light signal is applied through the skin of a patient suffering from fibromyalgia (FM), to a tender area, to stimulate a phototherapeutic response. In this case, the phototherapeutic response can include a biological response leading to the creation of a neural blockade to block nocioreceptive pathways to improve a subject's sensitivity to pain, thereby treating FM. The neural blockade, for example, can be due to the modulation of gene and/or protein expression associated with pain perception and sensitivity. For example, the gene and/or protein expression can be associated with the metabolism of neurotransmitters (e.g., catecholamines, serotonin, and the like). A gene associated with the metabolism of catecholamines (such as dopamine and norepinephrine) is catechol-O-methyltransferase (COMT), while a gene associated with the metabolism of serotonin is the serotonin transporter gene (5-HTT). Additionally or alternatively, the neural blockade can be aided by increased endorphin production, which act as ligands to downstream opioid-receptors to provide an inhibitory response. In addition, the neural blockade can be provided by a decrease in prostaglandin, which can provide pain regression. The neural blockade can also be due to an increase in blood flow dependent on an increase in nitric oxide to assist healing. The biological response can cause a reduction in the symptoms of fibromyalgia.

While not wishing to be bound by theory, there is strong evidence to suggest that one of the basic mechanisms of PBMT is the acceleration of electron transfer by electromagnetic radiation in the visible and near infrared region of the spectrum, via the modulation of cytochrome c-oxidase (CCO) activity. Traditionally, PBMT has attempted to modulate CCO activity using a single wavelength in the visible and near infrared region of the spectrum. However, the use of such single wavelengths cannot effectively modulate CCO activity since the single wavelength is limited by its specific absorption spectrum. The light signal used herein has a combination of wavelengths, which are used concurrently, providing an overlapping effect of peak activation, which accelerates CCO activity. Additionally, the time of CCO activation is prolonged across the entire therapeutic window by delivering much smaller doses across many wavelengths, rather than a single wavelength of a greater power. The multiple wavelengths enhance adenosine triphosphate (ATP) production, requiring less energy, and provides continual photodissociation of nitric oxide (NO), not only from CCO, but also from intracellular stores like nitrosylated forms of hemoglobin and myoglobin. NO is a potent vasodilator and PBMT can increase the vasodilation due to NO and increases the availability of oxygen to treated cells, and allows for greater traffic of immune cells into tissue, which counteracts inflammatory and immune responses and treats fibromyalgia.

Accordingly, the light signal of the present disclosure includes a combination of individual light waves. The combination enhances each individual wavelength's ability to penetrate the skin, to allow for a greater portion of the available light energy to reach biological targets beneath the surface. Accordingly, the light signal can be configured so that individual light waves (from chosen light sources, with a selected wavelength, with a given power, and the like) within the light signal work constructively to create a synergistic effect. The light signal can be delivered by a light source device that includes a combination of one or more super pulsed lasers (which deliver a desired peak power from an ultrashort pulse with a minimized level of heat accumulated in the patient's tissue), one or more infrared emitting diodes, and one or more light emitting diodes. In some instances, the light source device can include groups of a super pulsed laser, an infrared emitting diode, and a light emitting diode. In other instances, the light source device can include groups of a super pulsed laser, at least three infrared emitting diodes, and at least three light source devices. The use of a super pulsed source can minimize the photo-thermal effect accumulating within the skin surface and target tissue. Additionally, the light source device can include a permanent magnet to provide a static (or constant) magnetic field.

IV. Systems

One aspect of the present disclosure can include a system 10 (FIG. 1) that applies photobiomodulation therapy (PBMT) to a tender area in a subject who has been diagnosed with fibromyalgia (FM). In response to the PBMT, the tender area can undergo a phototherapeutic response, which can treat FM. For example, a subject can be diagnosed with FM, which is characterized by chronic, widespread musculoskeletal pain and can be accompanied by fatigue, sleep, memory, cognitive difficulties, mood issues, tension headaches, migraines, temporomandibular joint (TMJ) disorder, irritable bowel syndrome, interstitial cystitis or painful bladder syndrome, anxiety, and/or depression. The phototherapeutic response can lead to the creation of a neural blockade to block nocioreceptive pathways (in peripheral nerves within the tender area and/or within the brain or spinal cord), which can improve the subject's sensitivity to pain. Accordingly, the PBMT of the system 10 can counteract the characteristic widespread pain of FM and, in turn, reduce the other negative symptoms associated with FM, improving the subject's overall quality of life. While PBMT is a non-pharmacological therapy that can be used alone to treat fibromyalgia, PBMT can also be used in combination with a pharmaceutical treatment and/or an alternative treatment (like stress management or exercise) to treat FM.

The system 10 can include at least a light source device 11 that delivers the PBMT to the dystrophic muscle or muscle group and a controller 12 to deliver inputs to the light source device 11 related to the delivery of the PBMT via a wired connection and/or a wireless connection. The PBMT can be applied to the tender area by a light signal that is generated by a light source device 11. To facilitate the delivery of the light signal to the tender area, the light source device 11 can be shaped so that at least a portion makes contact with the subject's skin proximal to the tender area.

Figure 10:
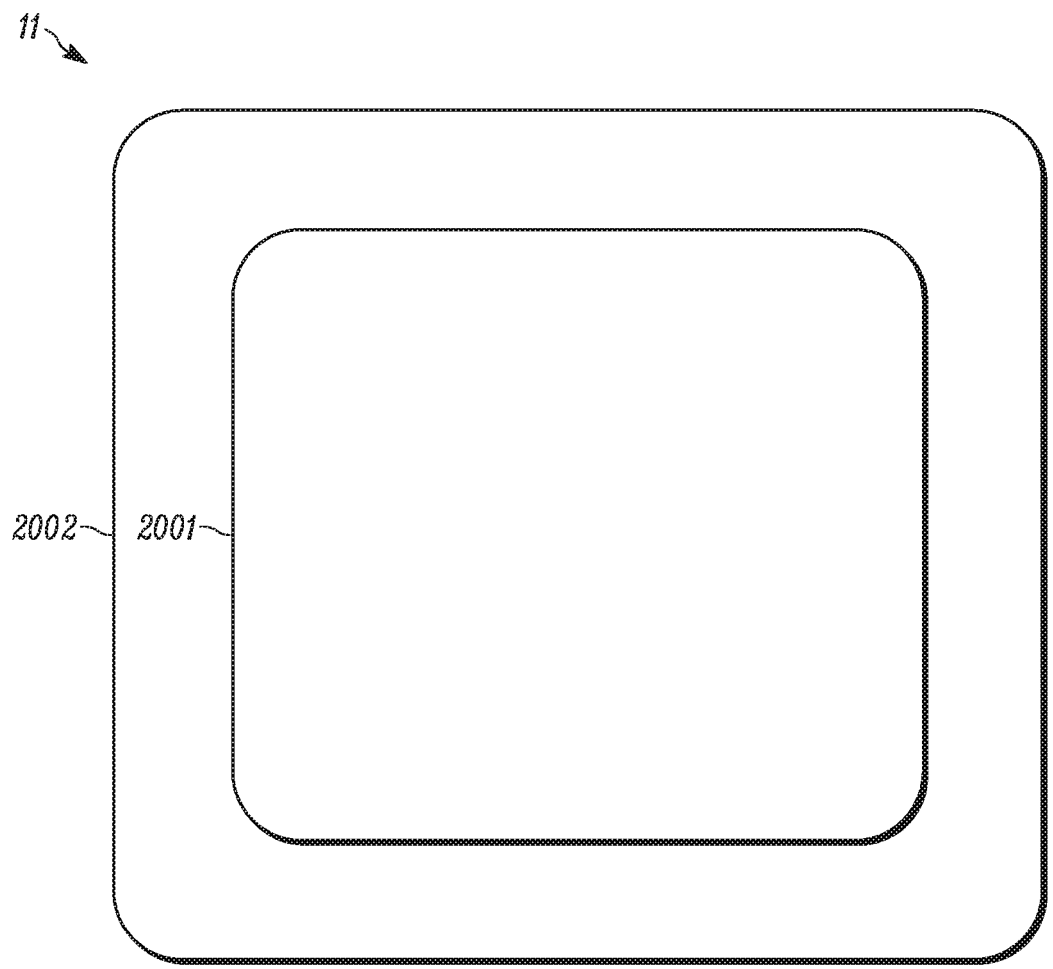
FIG. 10 shows a diagram of an example of the light source device of FIG. 1.

The light source device 11 can be configured in any shape that facilitates contacting a portion of the skin and/or the delivery of the light signal. An example of the light source device 11, including an electronics housing 2001 and a device housing 2002, is shown in FIG. 10. The electronics housing 2001 can include processing unit 14 and the power source and other electronics required for operation of the light source device 11. The device housing 2002 can surround the electronics housing and stabilize the electronics housing 2001. In some instances, the device housing 2002 can embody a securing mechanism to removeably secure the light source device 11 to an area of the subject's skin. For example, the securing mechanism can be able to be disconnected to facilitate movement of the light source device 11. Even in the absence of the securing mechanism, the light source device 11 can be portable with at least a portion being able to be moved to different areas of the subject's body. Light delivery source clusters 13 can be within the electronics housing 2001 and/or within the device housing 2002.

Figure 11:
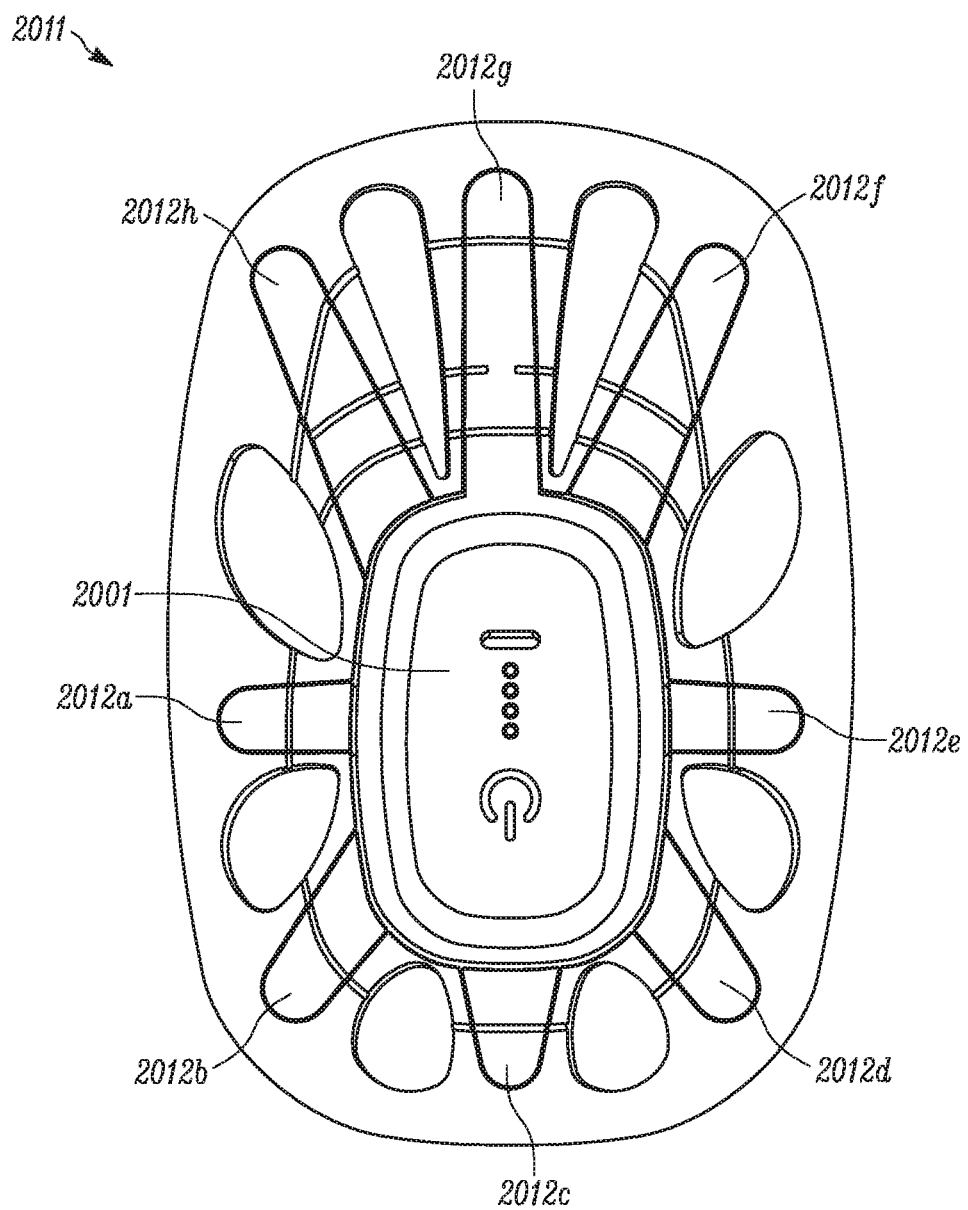
FIG. 11 shows a picture of another example of the light source device of FIG. 1.
Figure 12:
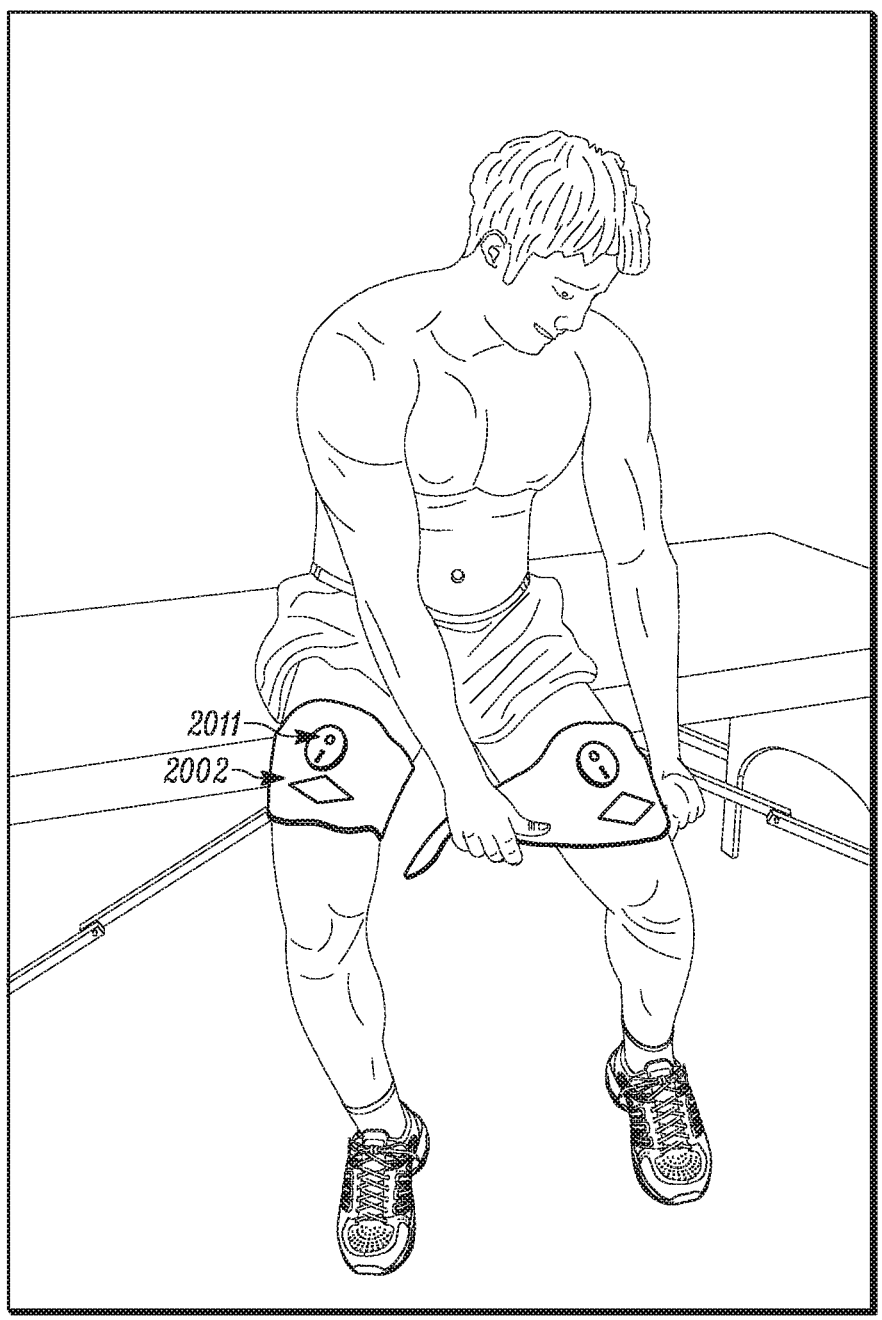
FIG. 12 shows a picture of an example use of the light source device shown in FIG. 1.

As one example, the light source device 11 can be embodied as an insert 2011 (shown in FIG. 11). The insert can include the electronics housing 2001 and a number of flanges 2012*a-h* extending from the device housing. Any number of flanges 2012*a-h* may exist, from 0 to N, where N is an integer limited only by the size of the insert. The electronics housing 2001 and/or the flanges can be made of a hard material (e.g., plastic) and/or a flexible material (e.g., silicone, rubber, neoprene, or the like) and configured with a shape or flexible into a shape that conforms to the target tender area. The insert can be inserted into a device housing 2002 as shown in FIG. 12. The device housing 2002 can be made of a flexible material (e.g., silicone, rubber, neoprene, or the like) and secured around an area of the subject's body that includes the tender area.

Figure 13:
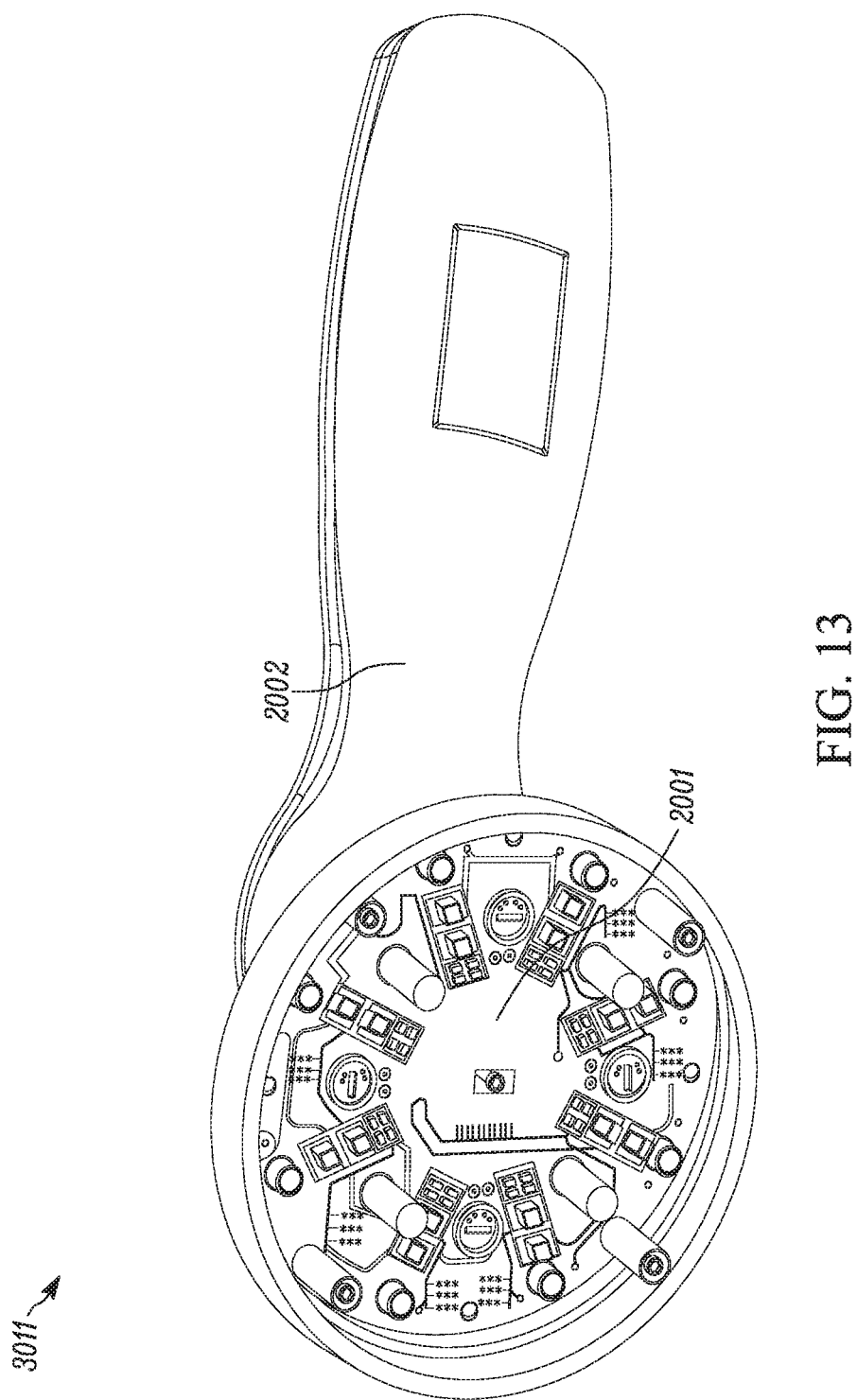
FIG. 13 shows a picture of another example of the light source device of FIG. 1.

As another example, the light source device 11 can be embodied as a probe device 3011 (FIG. 13). The probe device 3011 can include a device housing 22 that is made of a hard material (e.g., a plastic) and include a portion configured to contact the subject's skin proximal to the tender area at a 90-degree angle to deliver the light signal. The electronics housing 2001 can be housed within the device housing 2002 with at least the light delivery source clusters 13 being included in an area that contacts the skin. Another example, although not illustrated, can include a flexible array device with a portion shaped to contact the skin at a 180-degree angle to deliver the light signal.

The light source device 11 can include at least one light delivery source to generate the light signal at a certain wavelength, with a certain power, in an operating mode. The operating mode can be at least one of a pulsed operating mode, a continuous operating mode, and a super-pulsed operating mode. The light source device 11 can also include a processing unit 14 programmed (e.g., preprogrammed, programmed in response to an input from the controller 12 (which may be in response to an input), or the like) with a time for application of the light signal to the tender area (e.g., the time can be sufficient to stimulate the phototherapeutic response in the tender area). The processing unit 14 can also be programmed with the certain wavelength, the certain power, and/or the operating mode. In some instances, the light source device 11 can also include a permanent magnet to provide a static (or constant) magnetic field, which can be used to secure the light source device 11 to the area of the subject's skin and/or to affect the light signal. The constant magnetic field can be from 5 mT to 1 T. Additionally, the light source device 11 can also include a power source. The power source, in some instances, can be an internal battery. In other instances, the power source can receive and/or store power from an external source. In some instances, the external source can be associated with the controller 12.

In some instances, the light signal can include a light wave at a single wavelength of light delivered in a certain operating mode. However, in other instances, the light signal can include a combination of a plurality of individual light waves with different wavelengths of light delivered in two or more different operating modes. The combination of individual light waves is advantageous because the individual light waves can work constructively to create a synergistic effect, enhancing each individual wavelength's ability to penetrate the skin, allowing for a greater portion of the available light energy to reach biological targets beneath the surface of the skin.

Figure 2:
FIG. 2 is a block diagram illustration showing an example configuration of light sources within the light delivery source cluster of FIG. 1.

The plurality of individual light waves can be generated by a plurality of light delivery sources. Accordingly, the light source device 11 can include a plurality of light delivery sources, each configured to deliver light of a certain wavelength, with a given power, in a pulsed operating mode, a continuous operating mode, or a super-pulsed operating mode. One organization of the plurality of light delivery sources is in one or more light delivery source clusters 13 (an example of an individual cluster is shown in FIG. 2). In practice, the light source device can have any number of light delivery source clusters 13, limited only by the size of the area of the light source device 11 designated for delivery of the light signal.

As shown in FIG. 2, each light delivery source cluster 13 includes three types of light sources (LS1 15, LS2 16, LS3 17). However, the light delivery source clusters 13 may include a greater or fewer number of light sources. Three light sources are shown for simplicity of illustration and explanation. The light sources (LS1 15, LS2 16, LS3 17) each generate light waves with wavelengths within a wavelength range of 600-1100 nm (red to infrared). More particularly, LS1 15 can be configured to generate a first portion of the light signal with a wavelength from 890-910 nm (infrared); LS2 16 can be configured to generate a second portion of the light signal with a wavelength from 600-700 nm (red); and LS3 17 can be configured to generate a third portion of the light signal with a wavelength from 810-880 nm. In this example, LS1 15, which is in the middle of each light delivery source cluster 13, can operate in the super-pulsed operating mode, while LS2 16 and LS3 17, which surround LS1, can each operate in the continuous operating mode or the pulsed operating mode. In other words, LS1 can be a super pulsed laser that creates an impulse of high intensity that emits for a billionth of a second in synchrony with LS2 (a red source, like a red LED or a red light) and/or LS3 (an infrared source, like an infrared LED or an infrared light). Advantageously, the use of the super-pulsed laser (LS1) allows a desired peak power to be delivered for an ultrashort pulse with a minimized level of heat accumulated in the subject's skin and tender point (in other words, minimizes the photothermal effect).

Many configurations of each light delivery source cluster 13 are possible. Two examples of possible configurations are set forth, but countless other possibilities exist (including with other light sources), as long as there are one or more L1, one or more L2, one or more L3. One possible configuration of each light delivery source cluster 13 is a 1:1:1 configuration, with L1 (the super-pulsed laser) between L2 (the red source) and L3 (the infrared source). Another possible configuration of each light delivery source cluster 13 is a 1:3:3 configuration with L1 surrounded by three (or more)

L2 and three (or more) L3. For example, in this configuration, L2 and L3 can alternate as they are arranged around L1 (e.g., L2 L3 L2 L3 L2 L3 surrounding L1). As another example, L2 and L3 can be grouped together around L1 (e.g., L2 L2 L2 L3 L3 L3). Although not expressly described, other example configurations are possible in the 1:3:3 light delivery source cluster 13. The light delivery source clusters 13 within the same light source device 11 can be configured identically, but need not have identical configurations. For example, a light source device 11 can have three light delivery source clusters, with one a 1:1:1 configuration and the other two 1:3:3 configurations.

V. Methods

Another aspect of the present disclosure can include methods 30, 40 (FIGS. 3 and 4) for applying photobiomodulation therapy (PBMT) to a tender point in a subject who has been diagnosed with fibromyalgia. The methods 30, 40 can be executed by hardware—for example, at least a portion of the system 10 shown in FIG. 1 and described above. Additionally, PBMT provides a non-pharmacological therapy to patients suffering from fibromyalgia, which can be used alone or in combination with a pharmaceutical treatment or an alternative treatment (like stress management techniques or exercise) to treat fibromyalgia.

The methods 30 and 40 are illustrated as process flow diagrams with flowchart illustrations. For purposes of simplicity, the methods 30 and 40 shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30 and 40. Additionally, one or more elements that implement the methods 30 and 40, such as light source device 11 and/or controller 12 of FIG. 1, may include a non-transitory memory and one or more processors that can facilitate the configuration and generation of the light signal.

Figure 3:
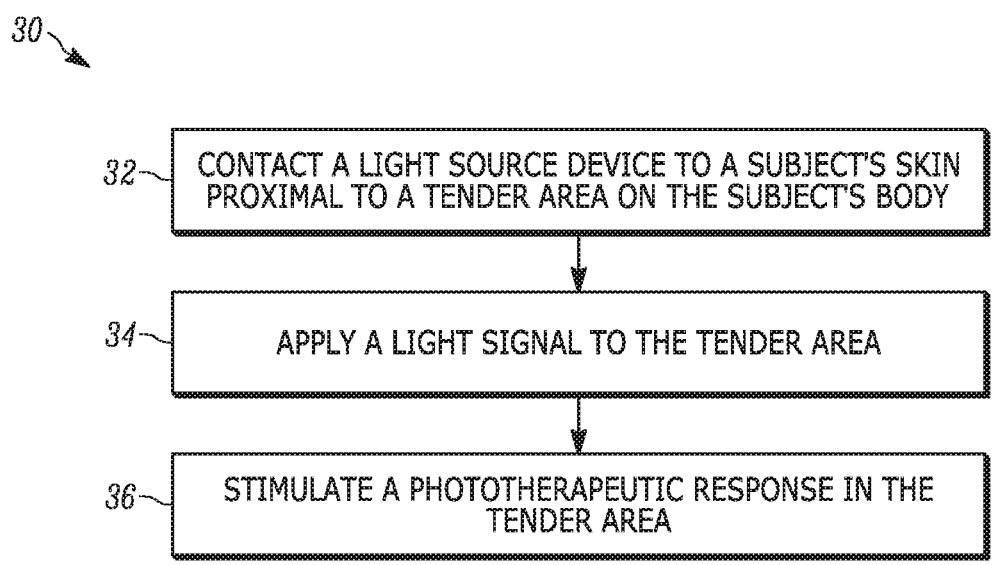
FIG. 3 is a process flow diagram of an example method for applying PBMT to a tender area on a subject's body to treat FM in accordance with another aspect of the present disclosure.
Figure 4:
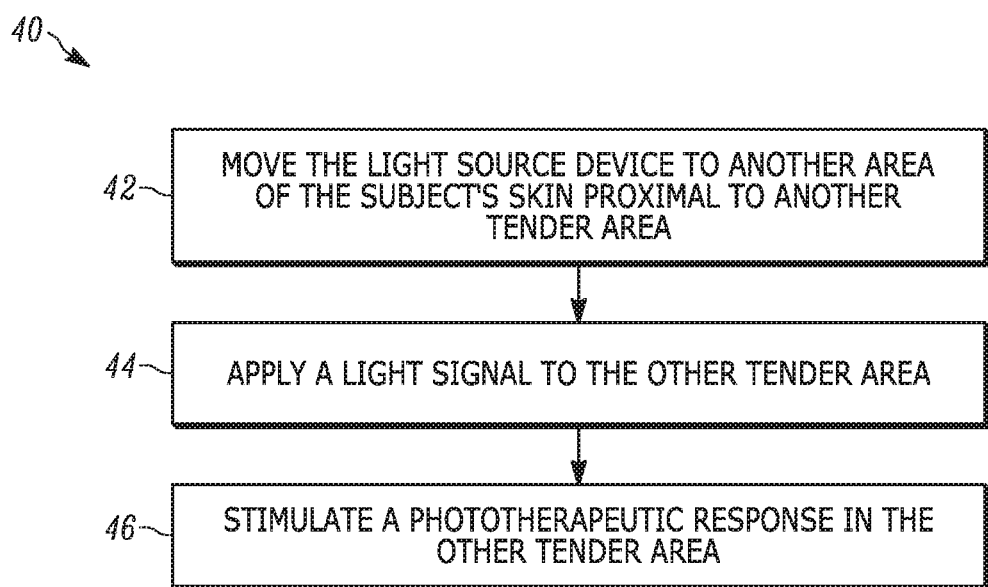
FIG. 4 is a process flow diagram of another example method for applying PBMT to another tender area on a subject's body to treat FM in accordance with a further aspect of the present disclosure.

Referring now to FIG. 3, shows a method 30 for applying PBMT to a tender area to treat FM. At step 32, a light source device (e.g. light source device 11) can be contacted to a subject's skin proximal to (e.g., directly adjacent or over) a tender area. The subject can be any patient who has been diagnosed with FM.

At step 34, a light signal can be applied to the tender point. The light signal can be generated in at least one of a pulsed operating mode, a continuous operating mode, and a superpulsed operating mode. The light signal can include one wave of a single wavelength. However, alternatively, the light signal can include a plurality of individual waves with multiple wavelengths. The combination of the plurality of individual waves can work constructively to create a synergistic effect, enhancing each individual wavelength's ability to penetrate the skin, allowing for a greater portion of the available light energy to reach biological targets beneath the surface of the skin. The light signal is applied for a time sufficient to stimulate a phototherapeutic response in the tender point. At step 36, a phototherapeutic response can be stimulated in the tender points. The phototherapeutic response can trigger a biological response leading to the creation of a neural blockade to block nocioreceptive pathways to improve a subject's sensitivity to pain, leading to an improvement in a subject's overall quality of life The method 30 continues in FIG. 4, which shows a method 40 that occurs after moving the light source device.

At step 42, the light source (e.g. light source device 11) can be moved to another area of the subject's skin proximal to another tender area. At step 44, a light signal can be applied to the other tender area. At step 46, a phototherapeutic response can be stimulated in the other tender area.

VI. Experimental

The following example is shown for the purpose of illustration only and is not intended to limit the scope of the appended claims. This experiment demonstrates the promise of photobiomodulation therapy (PBMT) as a non-pharmacological tool for treating fibromyalgia (FM). The PBMT provides a non-pharmacological treatment that does not present harmful side effects, making PBMT a promising tool for treating FM. Additionally, PBMT can be combined with exercise training (EXT) to further reduce pain and improve health-related quality of life as well as functional capacity.
Methods
Study Design and Sample The study was designed to address two main issues: (Set 1—acute) to investigate an immediate effect of a single session of phototherapy/EXT on chronic pain; (Set 2—chronic) to analyze a long-term (10 weeks) effect of the single session of phototherapy/EXT on chronic pain and other FM symptoms. Set 1 and Set 2 were distinct experiments and performed with independent volunteers.

The volunteers were patients from the three rheumatological centers with a FM diagnosis for an average of 5±9 years and evaluated for medical history, physical examination, and rheumatologic screening. The demographics of the volunteers are shown in Table 1.

TABLE 1

| Parameters for PBMT | | |
|---|---|---|
| | Set 1 | Set 2 |
| Age (years) | 35 ± 3 | 40 ± 2 |
| Height (m) | 1.58 ± 1 | 1.59 ± 1 |
| IMC (kg/m$^2$) | 26 ± 5 | 27 ± 4 |
| Race | | |
| Other or Biracial | 48 | 41 |
| White | 32 | 39 |
| Education | | |
| Elementary School | 14 | 9 |
| High School | 66 | 71 |
| Employment | | |
| Employed | 52 | 50 |
| Unemployed | 28 | 20 |
| Income (R$) | | |
| <10,000 | 9 | 4 |
| 10,000-30,000 | 67 | 75 |
| 30,000-50,000 | 4 | 2 |

Patients received FM diagnostic scores as reported by the American College of Rheumatology on Fibromyalgia Impact Questionnaire (FIQ). The Research Diagnostic Criteria (RDC) was applied aiming at sleeping-disturbed parameters. The recruitment period was from November 2014 to September 2016. The study was carried out according to the Declaration of Helsinki and was registered at ClinicalTrials.gov and approved by an ethics committee.

All participants reported to have maintained the usual pharmacological therapy. Most of the patients used different doses of paracetamol or amitriptyline, and hypnotics were the least used pharmacological class. There were no dropouts or exclusions following randomization nor any harm or unintended outcomes reported.

The inclusion criteria were women ≥35 years old, 5 years from FM diagnosis, optimized drug management, functionally and cognitive independence, full availability for study protocol, and no contraindication to exercise or/and phototherapy. The exclusion criteria were patients with contraindication to exercise or/and phototherapy, missing more than three treatment sessions, psychiatric disorders, missing teeth or use of dentures, history of face trauma or currently undergoing orthodontic intervention, and presence of any disorder that was confused with FM. Patients were followed through their regular health checkups and drug therapy was continued until the end of the study. The eligible participants were instructed not to change their lifestyles or pharmacological therapies during the study.

A total of 160 patients were eligible for the study. Half of these patients were randomly designated to participate in Set 1, and the other participants were designated to participate in Set 2. The patients in each group were randomly assigned, by an independent researcher, to one of the following groups: control (CON) (only under pharmacological treatment); phototherapy (PHO): patients submitted to phototherapy; exercise training (EXT): patients submitted to exercise training and phototherapy placebo (phototherapy device was turned off as a blinding procedure); phototherapy and exercise training (PHO EXT).

Blinding Procedure and Interventions

An independent researcher was responsible for programming the phototherapy device, which was turned on (phototherapy)/off (placebo) prior to application. A second researcher guided the exercise training and was blinded for phototherapy and/or placebo procedures. A third researcher was blinded to the allocation of patients and independently assessed the outcomes. The statistical analysis was performed by a fourth researcher, who was blinded to experimental groups. All patients were blinded to whether the laser device was in the on or off mode.

The follow-up intervention was 10 weeks, when patients underwent two treatment sessions for phototherapy, exercise, phototherapy/exercise, and placebo procedure per week, respectively (experimental Set 2). Phototherapy was applied 30 min prior to each exercise session or placebo procedure, and treatment sessions were carried out on Tuesdays and Thursdays. The outcome parameters were evaluated at baseline (prior group randomization) and 48 h after the last day of intervention. Similar intervention route was implemented to Set 1 design; however, only a phototherapy and/or an exercise session was conducted to analyze the impact on pain. These patients were evaluated at baseline and after 24 h.

Phototherapy

The multiple light sources (LLLT and LED) Pain Away/PainCure™ nine-diode cluster device (Multi Radiance Medical®, Solon, Ohio, USA) was applied to 10 tender points, which were reported for pain in all patients (occipital, cervical (near the C7), trapezius, supraspinatus, second costochondral joint, lateral epicondyle, gluteal/sacrum, greater trochanter, and medial knee border). The temporomandibular joint (TMJ, bilaterally) was also irradiated. Each point was irradiated for 300 s, and a 39.3-J total energy was delivered. Phototherapy device properties are shown in Table 2.

TABLE 2

Parameters for PBMT

| 1 Super-pulsed Infrared Laser Diode | |
| --- | --- |
| Wavelength (nm) | 905 |
| Frequency (Hz) | 1000 |
| Peak Power (W) | 8.5 |
| Average mean optical output (mW) | 0.9 |
| Power density (mW/cm$^2$) | 2.25 |
| Energy density (J/cm$^2$) | 0.75 |
| Dose (J) | 0.3 |
| Spot size of laser (cm$^2$) | 0.4 |
| 4 Red LEDs | |
| Wavelength (nm) | 640 (±10) |
| Frequency (Hz) | 2 |
| Average optical output (mW) - each | 15 |
| Power density (mW/cm$^2$) - each | 16.66 |
| Energy density (J/cm$^2$) - each | 5 |
| Dose (J) - each | 4.5 |
| Spot size of red LED (cm$^2$) - each | 0.9 |
| 4 Infrared LEDs | |
| Wavelength (nm) | 875 (±10) |
| Frequency (Hz) | 16 |
| Average optical output (mW) - each | 17.5 |
| Power density (mW/cm$^2$) - each | 19.44 |
| Energy density (J/cm$^2$) - each | 0.155, 0.447, or 1.497 |
| Dose (J) - each | 5.25 |
| Spot size of infrared LED (cm$^2$) - each | 0.9 |
| Cluster Probe | |
| Magnetic field (mT) | 35 |
| Irradiation time per site (s) | 300 |
| Total dose per site (J) | 39.3 |
| Aperture of device (cm$^2$) | 4 |
| Application mode | Cluster probe held stationary in skin contact at 90 degree angle and with slight pressure |

Exercise Training Protocol

The EXT consisted of stretching and aerobic exercise, twice a week, over 10 weeks. Active static stretching was carried out to induce mild discomfort in the following muscle groups: biceps, trapezius, latissimus dorsi, pectoralis, paraspinal, hamstrings, and quadriceps. Each stretching exercise was performed for three times of 30 s with a 30 s rest between each stretching, which shows to be a common rest interval for stretching exercises. Aerobic training was performed 30 min per session on motor drive movement (model LX-150) without inclination. The load exercise was 75% of age-predicted maximum heart rate (220-age (years)). Aerobic training was carried out on the bases of findings of improving the general symptoms, pain, and quality of life in women with fibromyalgia. Each aerobic exercise session was started immediately after the TMJ exercises.

Outcome Measures

General parameters: General parameters are age, body weight, body mass index, race, educational level, employment, in-come, marital status, and tender point count.

Overall clinical parameters: FIQ was a self-administered instrument to measure anxiety, depression, stiffness, and fatigue. RDC was carried out to determine sleeping disturbance, night awakenings, trouble sleeping, and mouth opening pattern.

Pain-Related Outcome

The pain threshold was analyzed with a digital algometer Instrutherm (DD-200 model). The rubber tip of the device (measuring 1 cm²) was placed in contact with the skin on specific FM tender points and TMA joints. A gradual pressure was applied until the patient reported feeling pain, and the displayed values were then recorded. The processes were executed only once to each point and a 30-s interval was given among the readings. Moreover, visual analog scale (VAS) consisting of a 10-cm rule was applied.

Quality of Life

Parameters were evaluated by a validated Brazilian version of the Medical Outcome study 36-item Short-Form Health Survey (SF-36). The following domains were assessed: physical functioning, role-emotional, role-physical, social functioning, mental health, vitality, and general health. The score ranged from 0 to 100, where a higher score represents a better quality of life.

Analysis

Data were analyzed with SPSS Statistics software, version 13.0. The Shapiro Wilk test was carried out to determine a data distribution. Comparisons among the groups were based on analysis of the magnitude of change from the baseline to the end of the interventions (Δ %). The comparisons were analyzed by the Kruskal-Wallis test and post hoc analysis by the Dunn test. The choice of test was established based on the data distribution.

Results

The following results demonstrate the acute and chronic repercussions of PBMT and EXT on pain sensitivity and quality of life of FM patients. The results indicate that the combination of super-pulsed laser and visible red and infrared LED therapy can significantly improve pain ratings in FM women.

Figure 5:
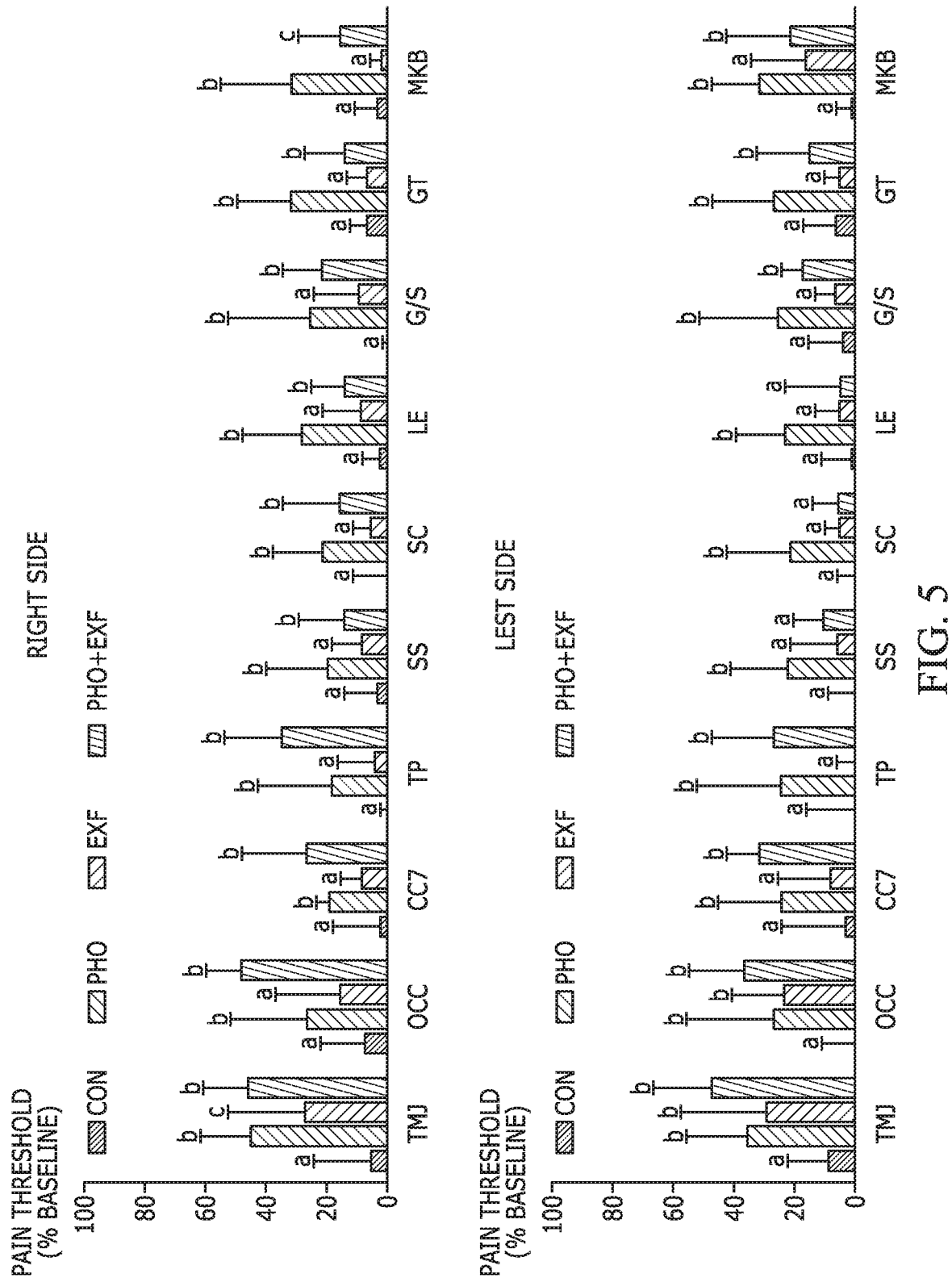
FIG. 5 shows graphs illustrating short-term effects of phototherapy and exercise training on pain threshold (different letters show significant differences among groups)
Figure 6:
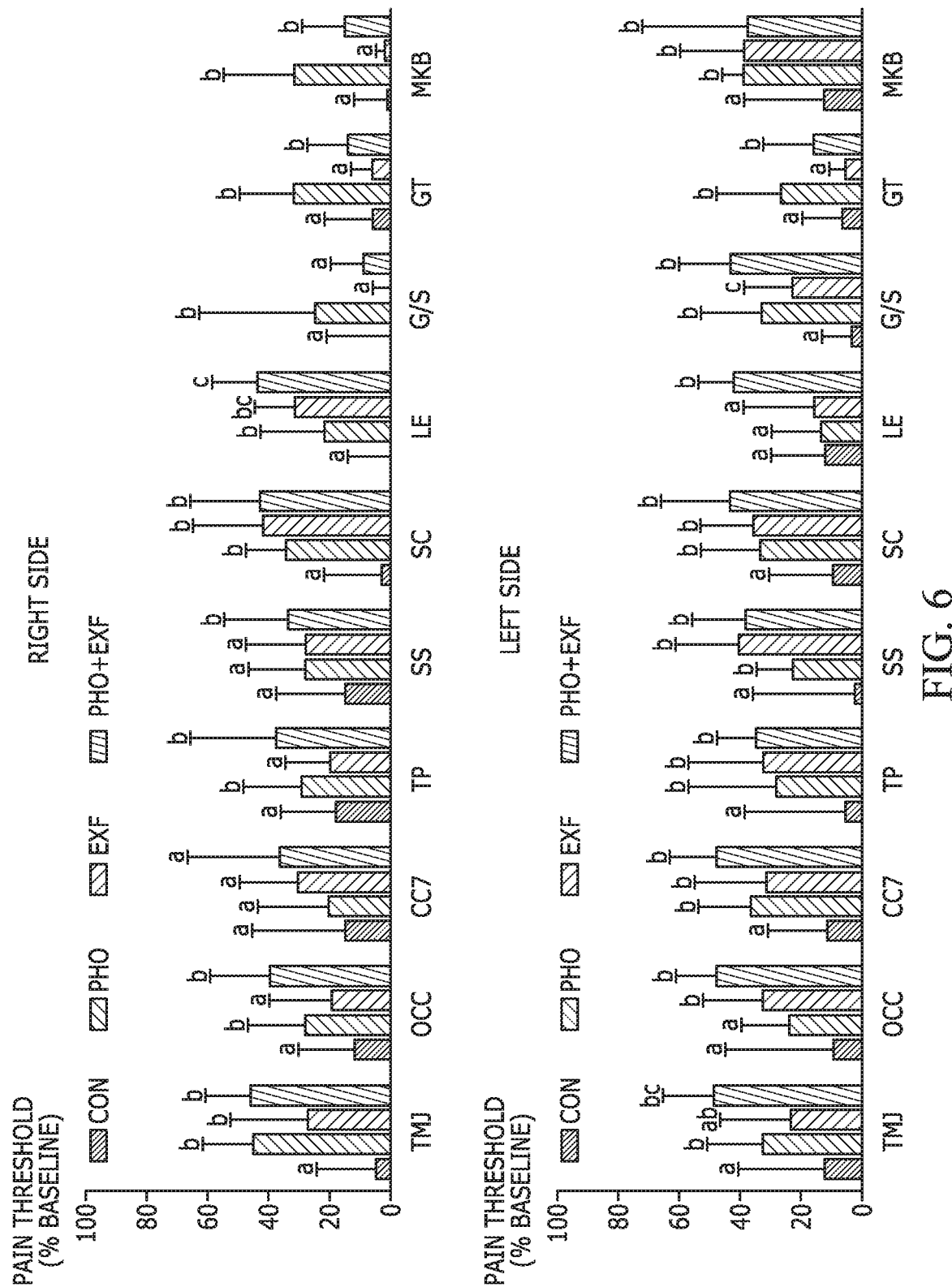
FIG. 6 shows graphs illustrating long-term effects of phototherapy and exercise training on pain threshold (different letters show significant differences among groups)

The experimental results for Set 1 are shown in FIG. 5. As shown, the pain threshold level was improved in the PHO group, with a mean difference (Δ %) in all tender points compared to CON group. There was no significant improvement in the pain threshold after an exercise session, except for cervical C7 region of the left body side. FIG. 6 also illustrates that there was no acute overlap effect of phototherapy and exercise on pain threshold.

Figure 7:
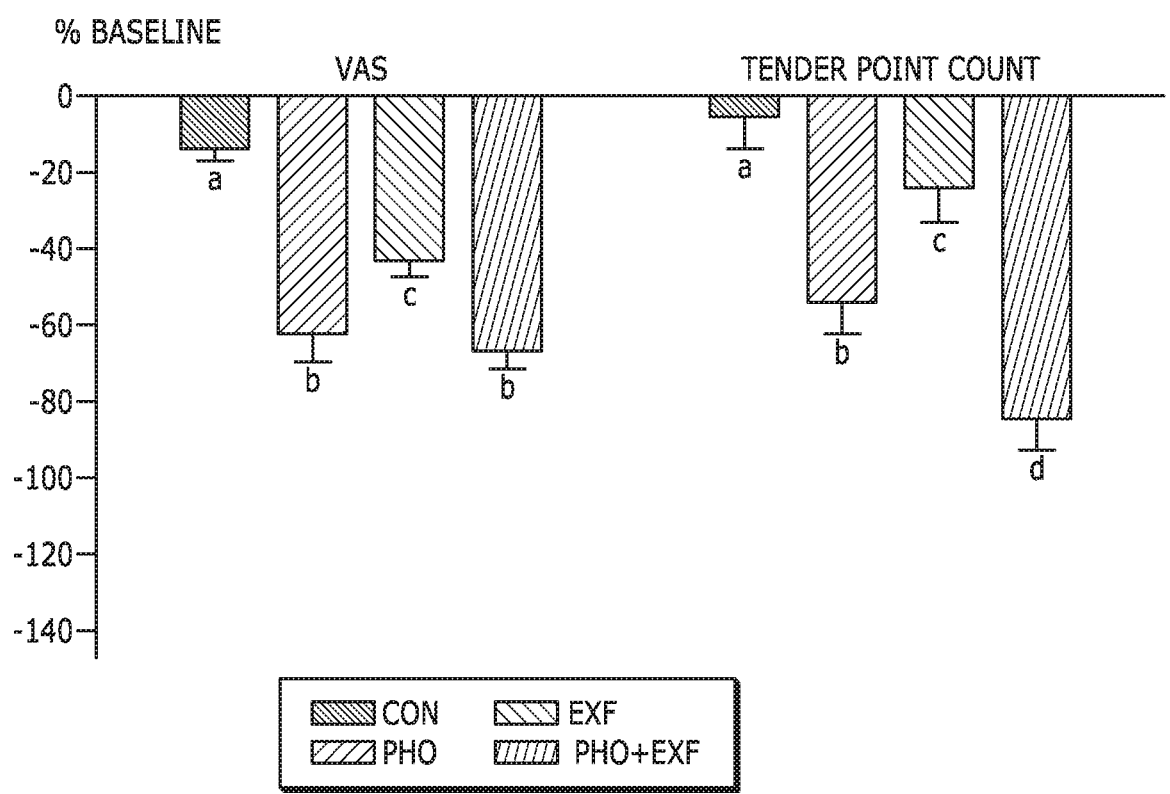
FIG. 7 shows a graph illustrating the long-term effect of phototherapy and exercise training on VAS scores and tender point numbers (different letters show significant differences among groups)

The experimental results for Set 2 are shown in FIG. 7, in which PHO group showed similar results to those reported in Set 1. Except for cervical and supraspinatus sites on the right body side and occipital and lateral epicondyle on the left body side, phototherapy improved the Δ % of pain threshold, with a mean difference compared to the CON group. In a different way to that observed in the Set 1, the data concerning the EXT group revealed improved pain threshold in several locations of the body. As depicted in FIG. 7, there were significant differences between EXT and CON in the Δ % values of right (points: TMJ; occipital; second condrocostal; lateral epicondyle) and left (points: occipital; cervical C7; trapezius; supraspinatus; second condrocostal; gluteal; medial knee border) body sides for the pain threshold. In the same way as in Set 1, no additional benefits were detected of the combination of phototherapy and exercise.

Figure 8:
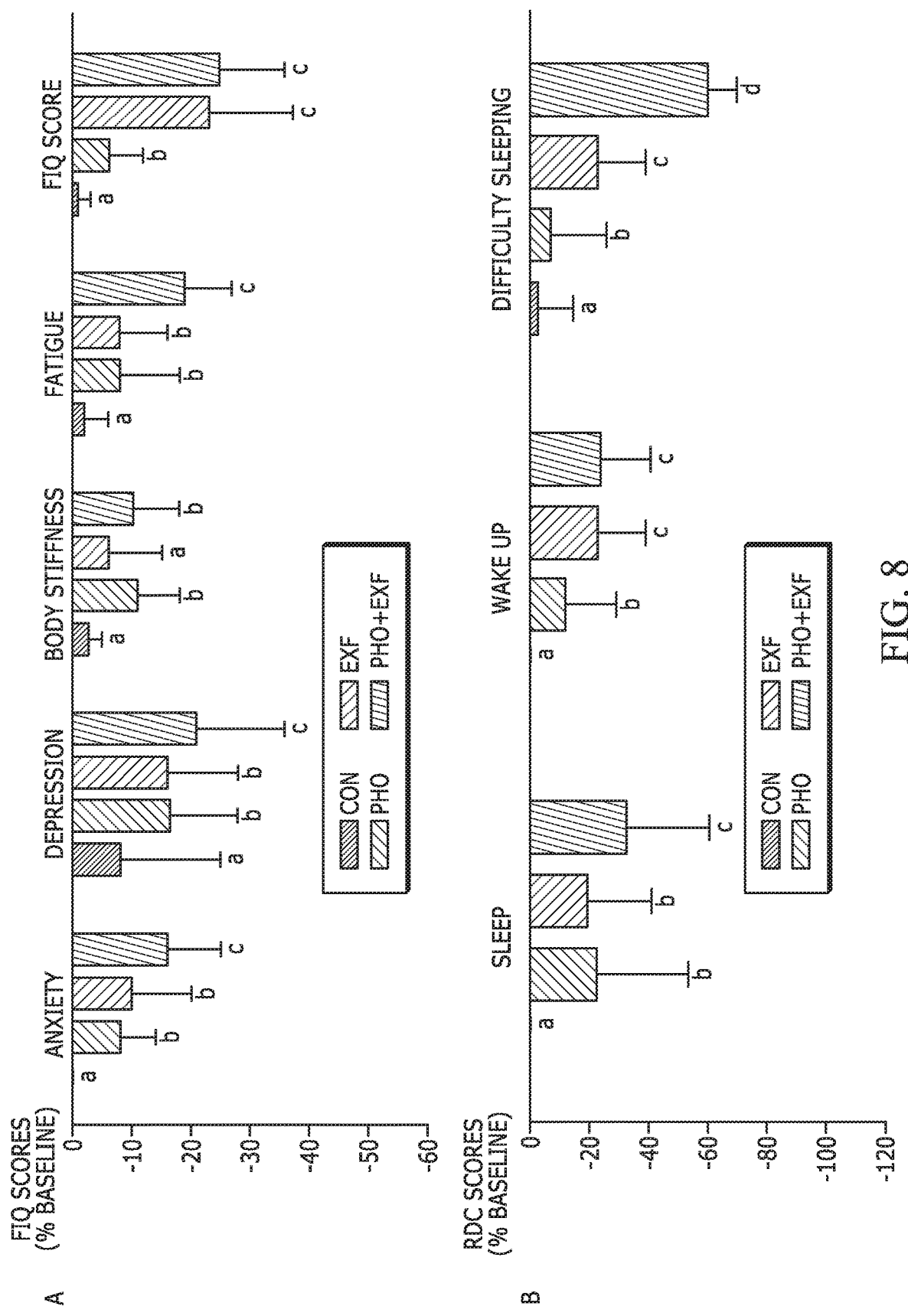
FIG. 8 shows graphs illustrating the long-term effect of phototherapy and exercise training on FIQ and RDC scores (different letters show significant differences among groups)

VAS was used to determine the pain perception in patients undergoing different interventions in Set 2 (FIG. 8). A large effect of phototherapy and exercise was observed, considering the post-treatment pain threshold change. Both PHO and PHO+EXT groups showed significantly greater pain reduction compared to CON and EXT groups, respectively. Another finding in FIG. 8 refers to the importance of the combined therapy to reduce the number of tender points. Thus, both PHO and EXT groups differed significantly from the CON group, a situation that was intensified in the combined therapy group.

Figure 9:
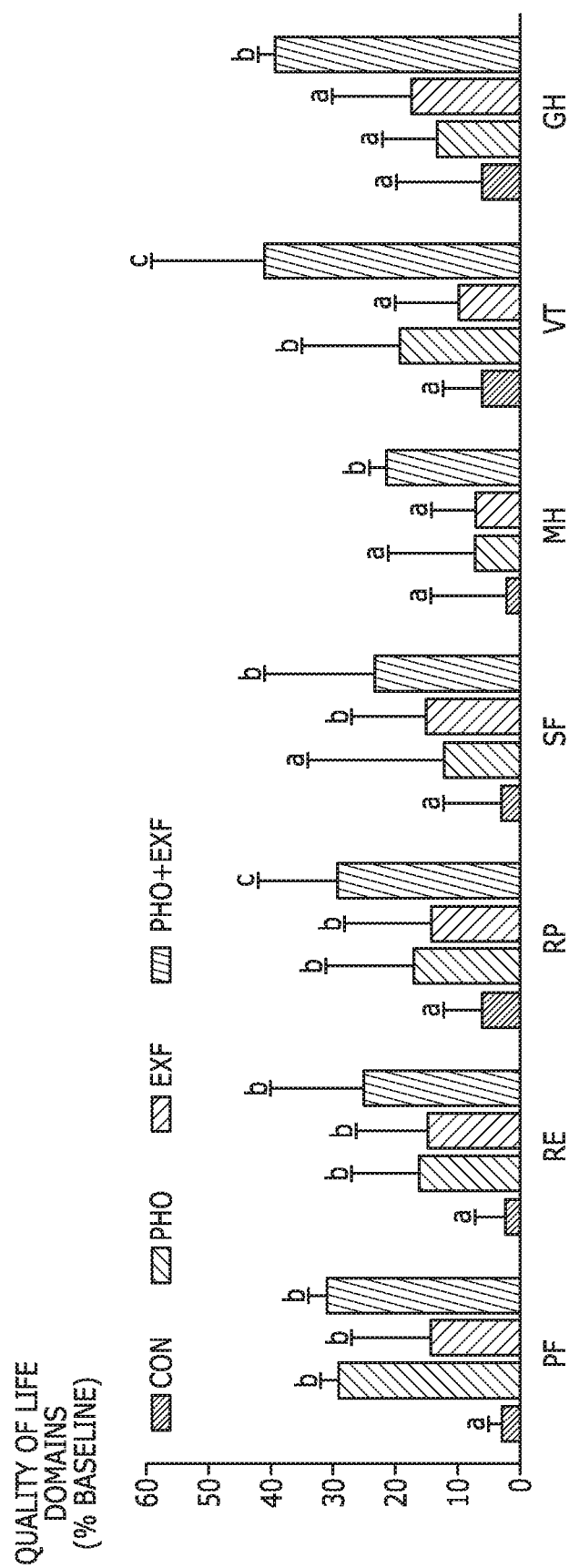
FIG. 9 shows a graph illustrating the long-term effect of phototherapy and exercise training on quality of life domains (different letters show significant differences among groups)

FIG. 9 summarizes overall clinical outcomes that were analyzed in Set 2. The combined therapies proved to be more effective, in which all the FIQ scores were significantly improved in the group PHO+EXT at the end of follow-up. Except for the "stiffness" variable in the EXT group, all values of Δ % were significantly higher in groups PHO, EXT, and PHO+EXT when compared to the CON group. Importantly, the beneficial role of combined therapy (Δ %) for anxiety, depression, and fatigue was significantly different in the PHO+EXT group compared to the other groups. Moreover, no significant differences were observed after pharmacological treatment on sleep quality markers and range of mouth opening (TMJ dysfunction marker associated to FM) in the CON group. Although the PHO group has shown a significant difference in the sleeping score and EXT group in the sleeping score and mouth opening, greater results were observed in the PHO+EXT, whereas significant differences were found in both variables and in difficulty falling sleep score. It is worth highlighting the comparisons among the groups in relation to Δ %: all parameters related to RDC exhibited values significantly superior in the PHO, EXT, and PHO+EXT compared to CON group. Furthermore, there was an additional effect of the combined therapy in sleeping and difficulty sleeping scores, whose values of Δ % were significantly higher in PHO+EXT than all the other groups.

As shown in FIG. 10, it was verified that the physical functioning, role-emotional, role-physical, and vitality were significantly higher in the PHO group compared to CON group. A similar finding was noticed in the EXT group, in which physical functioning, role-emotional, role-physical, and social functioning domains were improved in comparison with CON group. A higher benefit was derived from the combined therapy—role-physical, vitality, and general health domains were potentialized (Δ %) in the PHO-EXF group.

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The following is claimed:

1. A method comprising:
   contacting a light source device to a subject's skin proximal to a tender area on the subject's body; and
   applying a light signal through the light source device to the tender area, wherein the light signal is applied for a predetermined time to stimulate a phototherapeutic response in the tender area, wherein the light signal is applied to treat fibromyalgia,
   wherein the light source device comprises a first source configured to generate a first portion of the light signal with a wavelength from 890-910 nm, a second source configured to generate a second portion of the light signal with a wavelength from 600-700 nm, and a third source configured to generate a third portion of the light signal with a wavelength from 810-880 nm,
   wherein the first source operates in a super-pulsed operating mode, the second source operates in a pulsed operating mode or a continuous operating mode, and the third source operates in the pulsed operating mode or the continuous operating mode.

2. The method of claim 1, wherein the application of the light signal for the predetermined time improves at least one of a pain threshold, anxiety, depression, fatigue, and sleep of the subject.

3. The method of claim 1, wherein the light source device is a probe device or a flexible array device.

4. The method of claim 1, further comprising:
moving the light source device to another location on the subject's skin above another tender area in the subject's body; and
applying the light signal in at least one of the pulsed operating mode, the continuous operating mode, and the super-pulsed operating mode through the light source device to the other tender area, wherein the light signal is applied for another predetermined time to stimulate another phototherapeutic response at the other tender area, wherein the light signal is applied to treat fibromyalgia.

5. The method of claim 1, wherein the tender area is located in a low cervical region of the subject's body, a second rib of the subject's body, an occiput region of the subject's body, a trapezius muscle of the subject's body, a supraspinatus region of the subject's body, a lateral epicondyle region of the subject's body, a gluteal region of the subject's body, a greater trochanter region of the subject's body, and knee region of the subject's body.

6. The method of claim 1, wherein the first source comprises a super pulsed laser that creates an impulse of high intensity that emits for a billionth of a second in synchrony with the third source.

7. The method of claim 1, wherein the first source comprises a super-pulsed infrared laser source, the second source comprises a red light source, and the third source comprises an infrared light source.

8. The method of claim 7, wherein the second source further comprises at least three red light sources and the third source further comprises at least three infrared light sources.

9. The method of claim 7, wherein the light source device further comprises a permanent magnet that provides a constant magnetic field.

10. The method of claim 9, wherein the constant magnetic field is from 5 mT to 1 T.

11. The method of claim 1, wherein the light source device is a portable device comprising a power source.

12. The method of claim 1, wherein the light source device is removeably secured to the area of the subject's skin.

13. The method of claim 1, wherein the subject performs an aerobic exercise after allocation of the plurality of pulsed lights through the light source device to the tender area.

14. A light source device configured to contact a subject's skin above a tender point in the subject's body to treat fibromyalgia comprising:
a cluster of light delivery sources comprising:
a first light source configured to generate a first portion of a light signal with a wavelength from 890-910 nm in a super pulsed operation mode;
a second light source configured to generate a second portion of a light signal with a wavelength from 600-700 nm in a pulsed operating mode or a continuous operating mode; and
a third light source configured to generate a third portion of a light signal with a wavelength from 810-880 nm in a pulsed operating mode or a continuous operating mode,
a permanent magnet that provides a constant magnetic field from 5 mT-1 T;
a processing unit preprogrammed with a predetermined time for application of the light signal to the tender point in the subject's body to stimulate a phototherapeutic response in the tender point, wherein the light signal is applied to treat fibromyalgia; and
a power source.

15. The light source device of claim 14, wherein the first light source comprises a super pulsed laser that creates an impulse of high intensity that emits for a billionth of a second in synchrony with the third light source.

16. The light source device of claim 14, wherein the first light source comprises a super-pulsed infrared laser source, the second light source comprises at least two red light sources, and the third light source comprises at least two infrared light sources.

17. The light source device of claim 16, wherein the at least two red light sources comprise red light emitting diodes and the at least two infrared light sources comprise infrared light emitting diodes.

18. The light source device of claim 14, further comprising a securing mechanism to removeably secure the light source device to the area of the subject's skin.

19. The light source device of claim 14, wherein the predetermined time is 300 seconds.

* * * * *